United States Patent [19]

Bremer

[11] Patent Number: 5,549,620
[45] Date of Patent: Aug. 27, 1996

[54] BRAIN SURGERY WITH CRANIOTOMY PIN

[76] Inventor: Paul Bremer, 4550-1 Saint Augustine Rd., Jacksonville, Fla. 32207

[21] Appl. No.: 354,724

[22] Filed: Dec. 6, 1994

[51] Int. Cl.⁶ .................................................. A61B 17/04
[52] U.S. Cl. .............................. 606/151; 606/72; 411/338
[58] Field of Search ............................. 606/72, 232, 151, 606/219; 411/338

[56] References Cited

U.S. PATENT DOCUMENTS

| | | | |
|---|---|---|---|
| 2,118,561 | 5/1938 | Kleeberg | 411/338 |
| 2,485,531 | 10/1949 | Dzus et al. | 606/104 |
| 3,391,693 | 7/1968 | Georgiade et al. | |
| 4,026,276 | 5/1977 | Chubuck | |
| 4,031,569 | 6/1977 | Jacob | 606/232 |
| 4,233,979 | 11/1980 | Naser | |
| 4,275,490 | 6/1981 | Bivins | |
| 4,397,307 | 8/1983 | Keller | |
| 4,400,826 | 8/1983 | Preti et al. | |
| 4,444,179 | 4/1984 | Trippi | |
| 4,590,928 | 5/1986 | Hunt et al. | |
| 4,669,473 | 6/1987 | Richards et al. | 606/232 |
| 4,738,267 | 4/1988 | Lazorthes et al. | |
| 4,936,844 | 6/1990 | Chandler | 606/69 |
| 5,013,316 | 5/1991 | Goble et al. | 606/72 |
| 5,037,422 | 8/1991 | Hayhurst et al. | 606/72 |
| 5,046,513 | 9/1991 | Gatturna et al. | 606/232 |
| 5,064,425 | 11/1991 | Branemark et al. | 606/72 |
| 5,122,132 | 6/1992 | Bremer | 606/72 |

FOREIGN PATENT DOCUMENTS

| | | |
|---|---|---|
| 1353432 | 11/1987 | U.S.S.R. |
| 1421325 | 9/1988 | U.S.S.R. |
| 1655477 | 6/1991 | U.S.S.R. |

*Primary Examiner*—Gary Jackson
*Attorney, Agent, or Firm*—Nixon & Vanderhye P.C.

[57] ABSTRACT

A craniotomy pin is used to hold a flap of skull in place with respect to the surrounding skull after brain surgery. The pin is preferably an integral piece of biocompatible sterilizable material such as titanium or carbon fiber reinforced plastic. The head of the pin preferably comprises a first spherical segment having side reverse cut edges, and devoid of openings which can collect bacteria. The pin also includes a spherical segment locking portion, and a shaft connecting the head and locking portions. The shaft has a length less than the thickness of a human skull (e.g. about 3.5 mm or less). The locking portion preferably has sharp side edges and corners, and a sphere diameter and spherical extent less than that of the first spherical segment. The reverse cuts allow the head to be grasped with a tool and twisted when the shaft is in an elongated opening formed in the skull during brain surgery, so that the locking portion cuts into the skull and holds the skull flap to the surrounding skull. Typically at least three craniotomy pins at spaced locations are used to positively hold the skull flap in place.

20 Claims, 2 Drawing Sheets 5,549,620

BRAIN SURGERY WITH CRANIOTOMY PIN

BACKGROUND AND SUMMARY OF THE INVENTION

In most brain surgery it is necessary to open a large hole in the skull. The opening is typically made by forming two burr holes an inch or more apart, inserting a power cutting tool into one of the holes and making about a two inch diameter semicircular cut connecting the two burr holes together, and thereby forming a resulting flap of bone (skull). The skull flap is then bent out of the way, or broken out. After the brain operation the skull flap must be replaced and held in position until the skull heals. This is typically accomplished by drilling small pairs of holes in several places around the edge of the flap in the skull. Wire is then carefully threaded through the holes taking care not to tear the dural tissue covering the brain. The wires are then twisted together to secure the edges and the ends tucked into the cut opening so that they do not puncture the skin, which is then stitched into place over the skull flap. The procedure is long and involved and there always is the possibility of injuring the dura either by using the high speed drills that are necessary to form the small holes into which the wires is placed, or by the sharp points of the wire engaging the dura.

According to the present invention a method of holding a flap of skull in place after bone surgery is provided which minimizes the possibility of injury to the dura, and also cuts down the time of the skull flap affixing procedure (compared to the typical prior art procedure described above) by about twenty to thirty minutes. The invention also relates to a craniotomy pin which is utilized in practicing the method of the invention. The craniotomy pin (preferably at least three such pins being used) holds the skull flap in place with respect to the surrounding skull in a positive manner, can easily be covered by skin during the healing process, and is simple and easy to make and use.

According to one aspect of the present invention there is provided a method of holding a flap of skull in place after brain surgery, the flap of skull being separated from the surrounding skull by an elongated opening having first and second side edges spaced apart a distance X, using at least one craniotomy pin having a head with dimensions larger than X, and a locking portion having at least two cutting edges spaced a width greater than X and having a minor part with a dimension less than X, the cutting edges being spaced from the head a distance less than the thickness of the skull. The method comprises the steps of: (a) inserting the minor part of the pin into the opening, until the head substantially abuts the skull; and (b) twisting the head of the pin so as to cause the cutting edges to cut into the skull, one cutting edge cutting into the flap of skull and another cutting edge cutting into the surrounding skull, so as to lock the locking portion in place in the skull with the head engaging the top of the skull.

Step (b) may be practiced by twisting the head in a first direction, and there are the further steps, after step (b), of (c) allowing the skull to heal, and then (d) twisting the head of the pin in a second direction, opposite the first direction, to release the cutting edges from the skull, and then removing the pin from the skull. The head preferably has reverse cuts and is devoid of slots, sockets, or other openings which can collect bacteria. Steps (b) and (d) are practiced by gripping the head at the reverse cuts with the tool, and twisting the tool. Steps (a) and (b) are preferably practiced at at least three spaced locations along the elongated opening, to positively hold the skull flap in place with respect to the surrounding skull.

According to another aspect of the present invention a craniotomy pin is provided, comprising the following elements: A head having first and second longitudinal dimensions. A locking portion having first and second spaced cutting edges and having third and fourth longitudinal dimensions, at least the third longitudinal dimension being significantly less than the first dimension. And the head and the locking portion made of sterilizable biocompatible rigid material, the cutting edges capable of cutting into a human skull, to lock in the skull.

The fourth dimension is about 3 mm or less (e.g. 2 mm), and less than the second dimension. The head is devoid of slots, sockets, or other openings which can collect bacteria and includes a reverse cuts that are substantially parallel to each other and extend in the first dimension. In fact the head comprises first and second edges extending generally along the first dimension in which the reverse cuts are formed and third and fourth edges extending generally along the second dimension, the first dimension being longer than the second dimension, and the first through fourth edges all being curved. The locking portion cutting edges and the head are spaced from each other less than the thickness of a human skull, typically about 3.5 mm or less (e.g. typically a shaft extends between the head and the locking portion, and the head, shaft and locking portion are integral and made of titanium or carbon reinforced plastic) and typically have an angle of about 40–50 degrees (e.g. about 45 degrees) with respect to the second dimension.

According to another aspect of the present invention a craniotomy pin comprising an integral construction of biocompatible rigid material is provided which includes: A head comprising a first spherical segment having side reverse cut edges, and devoid of openings which can collect bacteria. A locking portion comprising a second spherical segment, having a sphere diameter less than that of the first spherical segment and a spherical extent less than that of the first spherical segment with sharp side edges and corners. And a shaft connecting the head and locking portion, the shaft having a length of about 3.5 mm or less.

It is the primary object of the present invention to provide simple and easy to construct and utilize a craniotomy pin, and method of holding a flap of skull in place after brain surgery using one or more such pins. This and other objects of the invention will become clear from an inspection of the detailed description of the invention and from the appended.

DETAILED DESCRIPTION OF THE DRAWINGS

Figure 1:
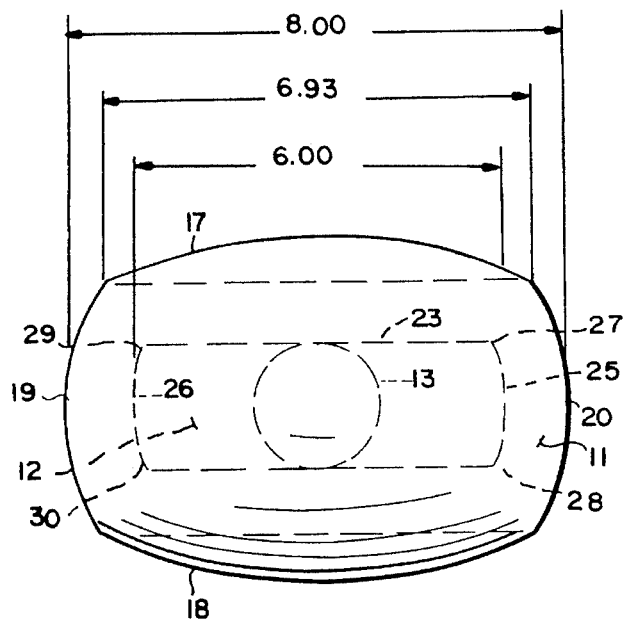
FIG. 1 is a top plan view of the craniotomy pin according to the present invention, the reverse cuts and locking portion thereof shown in dotted line.
Figure 2:
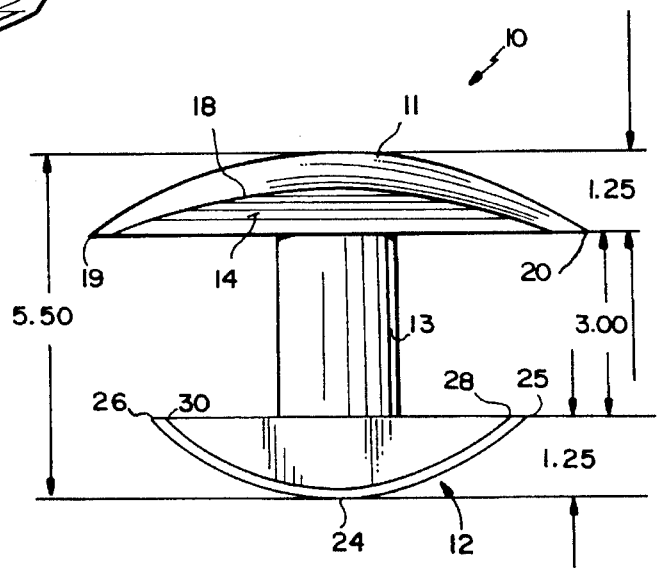
FIG. 2 is a side view of the pin of FIG. 1.
Figure 3:
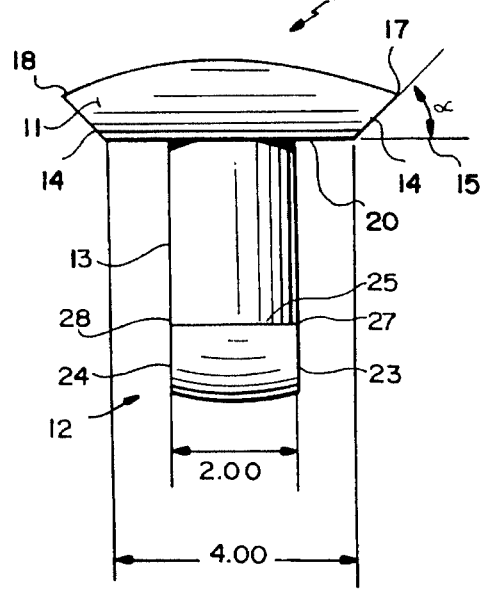
FIG. 3 is an end view of the pin of FIGS. 1 and 2.

FIGS. 1 through 3 schematically illustrate an exemplary craniotomy pin according to the present invention. In FIGS. 1 through 3 dimensions—in millimeters—for a preferred embodiment are shown. Pin 10 is of an integral piece of carbon reinforced plastic. If the pin 10 is made out of titanium, some of the dimensions can be slightly smaller, and the shapes can be different. For example, while spherical segment shapes of some portions are highly desirable if in carbon reinforced plastic, those same portions in titanium can be essentially flat.

In the preferred embodiment illustrated in FIGS. 1 through 3, the main components are a head 11, a locking portion 12, and a shaft 13 connecting and spacing the head 11 and locking portion 12. It is preferred that the components 11 through 13 be integral, although they may be separable and positively connected together. They are made of a biocompatible, relatively rigid, sterilizable material. While a number of different materials are suitable, titanium and carbon fiber reinforced plastic are preferred materials. Other potential materials include stainless steel, polyacrylates, or carbon-reinforced fiber plastic with titanium wings.

The head 11 preferably comprises a first spherical segment, as most clearly seen in FIGS. 2 and 3, which is devoid of openings (such as sockets or slots which are typically used for engaging fastener to twist it) because slots and sockets can easily collect bacteria. Rather than slots or sockets it includes side reverse cut edges 14 which are generally parallel to each other, disposed on opposite sides of the head 11. The head has a first dimension, indicated by the measurement arrows in FIG. 1, which preferably for the carbon fiber-reinforced plastic version is about 8 mm, and a second dimension—indicated generally as an imaginary line 15 in FIG. 3—substantially transverse to the first dimension. The reverse side cuts 14—as seen in FIG. 3—make an angle $\alpha$ with respect to the second dimension 15. The angle $\alpha$ is preferably between about 40–50 degrees, e.g. about 45 degrees as seen in FIG. 3.

The head 11 has first through fourth edges when viewed in plan (FIG. 1) 17 through 20, respectively, which are preferably curved as illustrated in FIG. 1. The bottom portions of the edges 17 through 20 are spaced from the top of the locking portion 12 a distance less than the thickness of a human skull. Preferably this spacing—which also essentially corresponds to the length of the shaft 13 is (as seen in FIG. 2),—is about 3.5 mm or less, preferably about 3 mm.

The shaft 13 may have any desired cross sectional configuration, with a maximum cross sectional dimension of less than the width "X" of an opening in the skull in which it is disposed. In the embodiment illustrated in FIGS. 1 through 3 the shaft 13 is shown with an octagonal cross section and with a maximum dimension of about 2.0 mm (see FIG. 3), the same as the width of the locking portion 12, which is about half the width (distance in dimension 15) of the lowermost portions of the head 11.

The locking portion 12 preferably comprises a second spherical segment, as seen in FIGS. 2 and 3, having a spherical diameter less than that of the first spherical segment (head 11), and a spherical extent less than that of the first spherical segment (head 11) too. The lesser spherical extent and spherical diameter are clear from FIGS. 1 through 3, and in the exemplary embodiment illustrated (as seen in FIG. 2) the spherical radius of the head 11 being about 7.02 mm, while the radius of the locking portion 12 is about 4.23 mm. The locking portion 12 also has sharp (cutting) side edges and corners. The side edges are illustrated by reference numerals 23 and 24, and are straight, and are connected together by end edges 25, 26 which are slightly curved (see FIGS. 1 and 3), but with the corners 27–30 being pointed (sharp).

While the dimensions of the locking portion 12 are typically less than those of the head 11, it is necessary that the length (indicated as about 6.00 mm in FIGS. 1 and 2) be greater than the width (2.00 mm as seen in FIGS. 1 and 3) by a significant amount. That is because when the locking portion is in one orientation with the width extending in and being received by an opening in the skull it does not lockingly engage the edges of the opening, but when it is twisted the points 27 through 30 and cutting edges 23 through 26 cut into the skull forming self locking of the pin 10 in place.

The embodiment illustrated in FIGS. 1 through 3 is relatively easy to construct, and simple to use, allowing positive positioning of the pin 10 without the need for any slots, sockets, or other openings in the head 11. Such openings are undesirable, simply collect bacteria, and also allow the thickness of the head 11 to be minimal so that the skin can more easily be fitted over it (e.g. it will not protrude through the skin), after it is installed in place. However, the head 11 has sufficient dimension so that it will prevent the pin 10 pulling through the skull, and will protect the skin. While what is illustrated in FIGS. 1 through 3 is presently a preferred embodiment, it should be understood that a wide variety of other constructions are possible. Any device which fits between the edges of the opening in the skull and the edges of the skull flap and cuts into both of the edges using the width of the kerf to produce an interference fit, will work. For example, although more difficult to manufacture and use than the embodiment illustrated in FIGS. 1 through 3, a short, fat screw with a 3–4 mm major diameter and a 1 mm minor diameter and double lead flat point would work.

Figure 4:
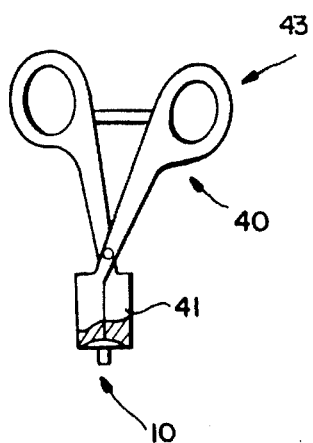
FIG. 4 is a side schematic view showing gripping of the craniotomy pin of FIGS. 1 through 3 with a tool using the reverse cuts of the pin.
Figure 5:
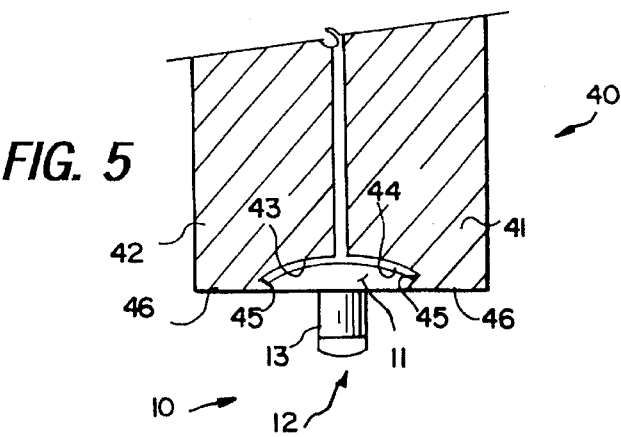
FIG. 5 is an enlarged schematic view of the gripping portion of the tool of FIG. 4 showing it holding the pin of FIGS. 1 through 3.

FIGS. 4 and 5 show how the pin 10 of FIGS. 1 through 3 is gripped for placement in the skull. The pin 10 is gripped by a hand tool 40 having jaws 41, 42 (see FIGS. 4 and 5) and a handle 43. The exact configuration of the tool 40 is not critical. One example of the tool that could be used is a conventional wire handling forceps with the jaws 41, 42 cut so that they fit the head 11 of the pin 10 as seen most clearly in FIG. 5. As seen in FIG. 5, each jaw 41 includes a generally spherical cutout 43 and an undercut portion 45 which engages the reverse cut surface 14 (see FIGS. 2 and 3 of the pin 10). The bottommost extent 46 of each of the jaws 41, 42 is substantially flush with the bottom edges of the head 11. In this way the head 11 is positively gripped for twisting action without the necessity for any slot or socket therein.

Figure 6:
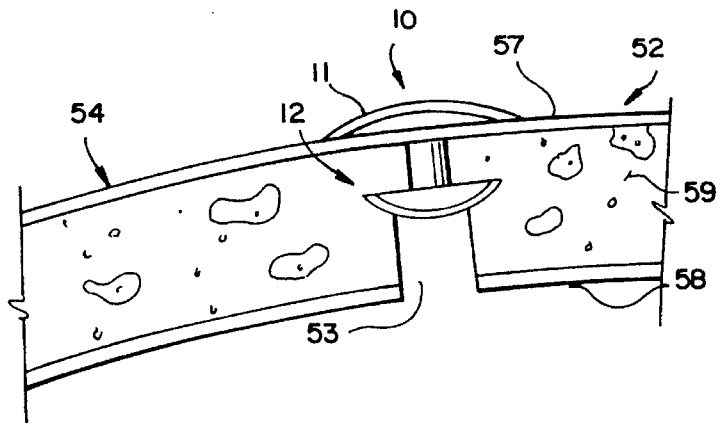
FIG. 6 is a side view, partly in cross section and partly in elevation, showing the pin of FIGS. 1 through 3 after it is twisted into locking position holding the flap of skull to surrounding skull.

The installation of the pins 10 will be described primarily with respect to FIGS. 6 and 7, but also referencing FIGS. 4 and 5. The pins 10 are installed after brain surgery. In typical brain surgery, burr holes 50, 51 are formed in the skull 52 (see FIG. 7), and then a cutting tool is inserted into one of the holes 50, 51 and used to form the elongated, generally semicircular, opening 53 which is typically of a diameter of about 2 inches, and connects the holes 50, 51. The skull flap 54 which is formed in the surrounding skull 52 is then bent back about the bone connection 55 between the openings 50, 51, or the flap 54 is detached, the bone line 55 either being broken or cut. This allows access to the brain within the skull 50, underneath the flap 54. After the bone surgery is performed, the flap 54 is either bent or inserted back in place so that the edges forming the opening 53 are adjacent each other, as seen in both FIGS. 6 and 7.

The opening 53 has a width X (the spacing between the side edges forming the opening 53) which is a dimension which is greater than the width of the shaft 13 and locking portion 12 (which have a dimension of about 2.0 mm as seen in FIG. 3).

A pin 10 is gripped by the tool 14, with the undercut portions 45 engaging the reverse cut surfaces 14, and inserted so that the shaft 13 and locking portion 12 are within the opening 53, slightly spaced from or lightly engaging the side edges forming the opening 53 in the skull surrounding area 52 and the skull flap 54. At this point the locking portion 12 is between the hard outer table 57 and hard inner table 58 of the skull 52, aligned with the softer bone 59 between the tables 57, 58 (see FIG. 6), of both the surrounding skull 52 and the skull flap 54. Then the operator simply twists the tool 40 by twisting the handle 43, and this causes the locking portion 12 to be twisted so that—depending upon the direction of twist—either the points 28, 29, or the points 27, 30 cut into the bone 59, the edges 23–26 also cutting into the bone 59, forming an interference fit which tightly holds the pin 10 in self locking position in place holding the flap 54 in the surrounding skull 52 in positive location with respect to each other, which facilitates healing.

Figure 7:
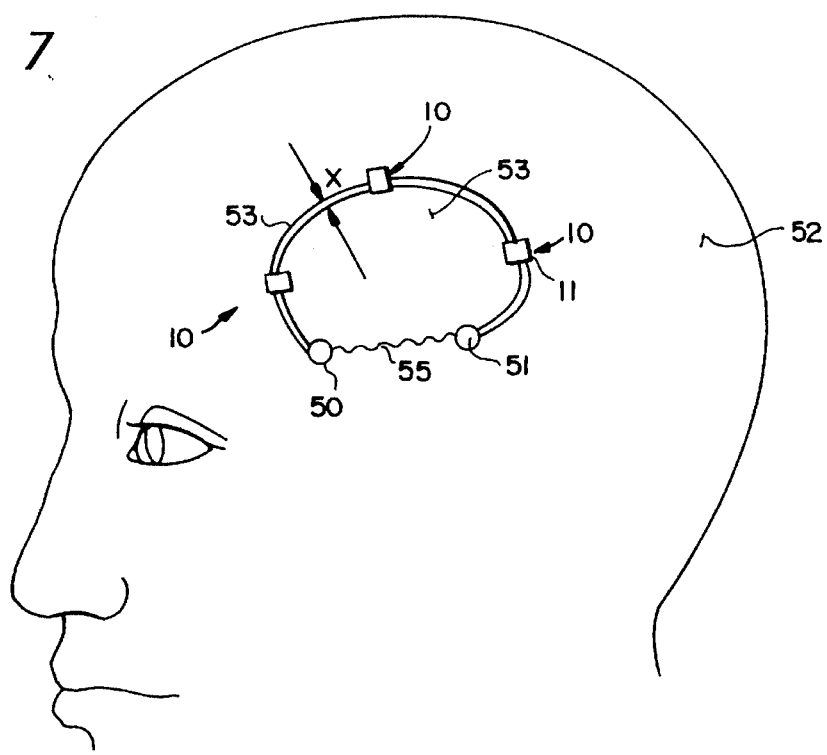
FIG. 7 is a side schematic view showing a plurality of pins such as illustrated in FIG. 6 showing a skull flap in place after brain surgery.

In a typical situation—as seen in FIG. 7—at least three of the pins 10, spaced from each other along the opening 53, are provided to positively hold the flap 54 in place with respect to the surrounding skull 52. Utilizing the pins 10, the possibility of the dura being injured during the affixing operation are minimal, there is no necessity to form wire-receiving openings using high a speed drill, nor the possibility of the wire puncturing the dural tissue. Also, the installation procedure associated with three or more pins 10 takes much less time than the prior art wire fastening procedure, typically about 20–30 minutes less.

The pins 10 may be constructed so that they can remain in place in the skull 52 even after healing, or they can be removed typically by making small incisions in the skin (which heals over the pins 10) to again place the tool 40 jaws 41, 42 engaging the reverse cuts 14, and then twisting in a direction opposite the direction that it was twisted when locking the pins 10 in place, and then pulling the pins 10 out.

It will thus be seen that according to the present invention a highly desirable method of holding a flap of skull in place after brain surgery, and a craniotomy pin for that purpose, have been provided. While the invention has been herein shown and described in what is presently conceived to be the most practical preferred embodiment thereof, it will be apparent to those of ordinary skill in the art that many modifications may be made thereof within the scope of the invention, which scope is to be accorded the broadest interpretation of the appended claims so as encompass all equivalent methods and devices.

What is claimed is:

1. A method of holding a flap of skull in place after brain surgery, the flap of skull being separated from the surrounding skull by an elongated opening having first and second side edges spaced apart a distance X, using at least one craniotomy pin having a head with dimensions larger than X, and a locking portion having at least two cutting edges spaced a width greater than X and having a minor part with a dimension less than X, the cutting edges being spaced from the head a distance less than the thickness of the skull; said method comprising: the steps of:

(a) inserting the minor part of the pin into the opening, until the head substantially abuts the skull; and (b) twisting the head of the pin so as to cause the cutting edges to cut into the skull, one cutting edge cutting into the flap of skull and another cutting edge cutting into the surrounding skull, so as to lock the locking portion in place in the skull with the head engaging the top of the skull.

2. A method as recited in claim 1 wherein step (b) is practiced by twisting the head in a first direction; and comprising the further steps of, after step (b), (c) allowing the skull to heal, and then (d) twisting the head of the pin in a second direction, opposite the first direction, to release the cutting edges from the skull, and then removing the pin from the skull.

3. A method as recited in claim 2 wherein the head has reverse cuts and is devoid of slots or sockets; and wherein steps (b) and (d) are practiced by gripping the head at the reverse cuts with a tool, and twisting the tool.

4. A method as recited in claim 3 wherein steps (a) and (b) are practiced at at least three spaced locations along the elongated opening, to positively hold the skull flap in place with respect to the surrounding skull.

5. A method as recited in claim 1 wherein the head has reverse cuts and is devoid of slots or sockets; and wherein step (b) is practiced by gripping the head at the reverse cuts with a tool, and twisting the tool.

6. A method as recited in claim 1 wherein steps (a) and (b) are practiced at at least three spaced locations along the elongated opening, to positively hold the skull flap in place with respect to the surrounding skull.

7. A craniotomy pin comprising:

a head having first and second longitudinal dimensions;

a locking portion having first and second spaced cutting edges and having third and fourth longitudinal dimensions, at least said third longitudinal dimension being significantly less than said first dimension;

a rigid connection between said head and said locking portion; and said head, connection, and locking portion all made of sterilizable biocompatible rigid material, said cutting edges capable of cutting into a human skull, to lock in the skull.

8. A craniotomy pin as recited in claim 7 wherein said fourth dimension is about a maximum of 3 mm, and less than said second dimension.

9. A craniotomy pin as recited in claim 8 wherein said head is devoid of slots, sockets, or other openings which can collect bacteria.

10. A craniotomy pin as recited in claim 9 wherein said head includes a pair of reverse cuts that are substantially parallel to each other and extend in said first dimension.

11. A craniotomy pin as recited in claim 10 wherein said cutting edges and said head are spaced from each other a distance of less than the thickness of a human skull.

12. A craniotomy pin as recited in claim 11 wherein said cutting edges and said head are spaced from each other a distance of which is a maximum about 3.5 mm.

13. A craniotomy pin as recited in claim 12 wherein said head comprises first and second edges extending generally along said first dimension in which said reverse cuts are formed, and third and fourth edges extending generally along said second dimension, said first dimension longer than said second dimension.

14. A craniotomy pin as recited in claim 13 wherein said first through fourth edges are all curved.

15. A craniotomy pin as recited in claim 7 wherein said connection comprises a shaft which extends between said head and said locking portion, said shaft having a length less than the thickness of a human skull.

16. A craniotomy pin as recited in claim 15 wherein said head, shaft, and locking portion are integral and are made of titanium or carbon fiber reinforced plastic.

17. A craniotomy pin as recited in claim 15 wherein said head is devoid of slots, sockets, or other openings which can collect bacteria.

18. A craniotomy pin as recited in claim 17 wherein said head includes a pair of reverse cuts that are substantially parallel to each other and extend in said first dimension.

19. A craniotomy pin as recited in claim 18 wherein said reverse cuts have an angle of about 40–50 degrees with respect to said second dimension.

20. A pin for medical use comprising an integral construction of biocompatible rigid material, including:

a head comprising a first spherical segment having side reverse cut edges, and devoid of openings which can collect bacteria;

a locking portion comprising a second spherical segment, having a sphere diameter less than that of said first spherical segment and a spherical extent less than that of said first spherical segment with sharp side edges and corners; and a shaft connecting said head and locking portion, said shaft having a maximum length of about 3.5 mm.

* * * * *